United States Patent
Müller et al.

(10) Patent No.: US 6,967,297 B2
(45) Date of Patent: Nov. 22, 2005

(54) SENSOR FOR DETECTING BELT RUPTURE

(75) Inventors: Heinrich Müller, Tuttlingen (DE); Manfred Lonau, Rietheim-Weilheim (DE)

(73) Assignee: Marquardt GmbH, Rietheim-Weilheim (DE)

( * ) Notice: Subject to any disclaimer, the term of this patent is extended or adjusted under 35 U.S.C. 154(b) by 0 days.

(21) Appl. No.: 11/029,026

(22) Filed: Jan. 4, 2005

(65) Prior Publication Data

US 2005/0161310 A1    Jul. 28, 2005

Related U.S. Application Data

(63) Continuation of application No. PCT/DE03/02298, filed on Jul. 9, 2003.

(30) Foreign Application Priority Data

Jul. 10, 2002    (DE) ................................ 102 31 078

(51) Int. Cl.⁷ .............................................. H01H 9/00
(52) U.S. Cl. ........................... 200/61.58 B; 200/61.18; 280/808; 340/686
(58) Field of Search ........... 200/61.58 B, 61.14–61.18, 200/532, 543–546; 340/686–687; 180/268; 280/801, 804–808

(56) References Cited

U.S. PATENT DOCUMENTS

| 3,890,720 A |   | 6/1975  | Nichols               |
|-------------|---|---------|-----------------------|
| 4,086,707 A | * | 5/1978  | Bochan ........................ 34/554 |
| 4,163,128 A | * | 7/1979  | Miskowicz ........... 200/61.58 B |
| 4,488,363 A |   | 12/1984 | Jackson et al.        |
| 4,771,148 A | * | 9/1988  | Bersonnet ............ 200/61.58 R |
| 4,866,223 A | * | 9/1989  | Collins et al. ........... 200/61.16 |
| 4,996,395 A | * | 2/1991  | Tada .................... 200/61.58 B |
| 5,821,488 A | * | 10/1998 | Falcon ..................... 200/52 R |
| 6,002,325 A | * | 12/1999 | Conaway ................. 340/384.1 |

FOREIGN PATENT DOCUMENTS

| DE | 8 915 158 U1 | 12/1989 |
| EP | 0 110 318 A1 | 6/1984 |
| GB | 389471 A | 6/1960 |

* cited by examiner

*Primary Examiner*—Richard K. Lee
(74) *Attorney, Agent, or Firm*—Burr & Brown

(57) ABSTRACT

A sensor for detecting a rupture or length change in a belt. The sensor has a movable transmission element operatively connected to the belt, that acts on an electrical switch having a contact system in the event of a length change or rupture of the belt. The contact system comprises a switching contact with a contact surface arranged on a first end, and an associated fixed contact. The transmission element acts on the second end of the leaf spring. A limb extends approximately from the first end of the leaf spring in the direction of the second end, and a further limb extends from the second end of the leaf spring in the direction of the first end. The free ends of the two limbs are clamped offset from one another on a carrier part of the switch, such that the switching contact switches over in a bistable manner.

16 Claims, 5 Drawing Sheets

2

SENSOR FOR DETECTING BELT RUPTURE

CROSS REFERENCE TO RELATED APPLICATIONS

This application is a continuation of International Application No. PCT/DE2003/002298, having an international filing date of Jul. 9, 2003, which designated the United States, the entirety of which is incorporated herein by reference.

This application also claims the benefit of German Application No. 102 31 078.5, having a filing date of Jul. 10, 2002, the entirety of which is incorporated herein by reference.

FIELD OF THE INVENTION

The invention relates to a sensor for detecting rupture and/or a length change in a belt. More specifically, the invention relates to a sensor with a movable transmission operatively connected to the belt that acts on an electrical switch in the event of a length change or rupture of the belt.

BACKGROUND OF THE INVENTION

In domestic electrical appliances, such as in a tumble dryer, a washing machine or the like, the drum is driven by means of an electric motor via a drive belt. The drive belt is a wearing part, so that the rupture or the fracture and/or an impermissible lengthening of the belt has to be monitored so as to initiate appropriate measures such as to switch off the electric motor in good time.

A sensor disclosed by EP 0 110 318 A1 for detecting a rupture in a belt is equipped with a movable transmission element which, within a belt tensioning device, is operatively connected to the belt, and with an electrical switch having a contact system. The transmission element in this case acts on the electrical switch in such a way that the contact system switches over in the event of an impermissible length change and/or rupture of the belt.

A conventional switch is used as the electrical switch in this sensor. It has transpired that the tolerances occurring in the belt length and with regard to the switching point in the switch are critical. This can lead to the sensor not operating in a functionally reliable manner. In the event of impermissible lengthening of the belt, there is additionally the danger that the switch will be actuated extremely slowly and (in particular when the conventional switch is used) in the event of remaining shortly before the switching point, will be operated in the region of a contact force of zero. As a result, an uncertain switching state is produced, as is the danger of contact welding. In addition, there is a danger of multiple switching on and off during operation in this limiting range as a result of a slight to and fro movement of the tensioning device.

SUMMARY OF THE INVENTION

The invention is based on the object of specifying a sensor for detecting rupture and/or a length change in a belt with a lower tolerance sensitivity.

In a sensor of the generic type, this object is achieved by a sensor having a movable transmission element operatively connected to the belt and an electrical switch having a contact system.

The contact system comprises a leaf spring with a switching contact having a contact surface and an associated fixed contact. The contact surface of the switching contact is arranged on a first end of the leaf spring, while the transmission element acts on the other, second end of the leaf spring. A limb that is free on one side extends approximately from the first end of the leaf spring in the direction of the second end and, in turn, a further limb that is free on one side extends from the second end of the leaf spring in the direction of the first end. The free ends of the two limbs are in each case clamped in with an offset from each other to a carrier part of the switch, such that the switching contact of the contact system switches over in the manner of a cascade and in particular in a bistable manner.

The solution as claimed in the invention avoids the aforementioned disadvantages, in that a particular bistable snap-action system with a cascade is used as the contact system. By means of the offset of the two clamped points on the carrier part, the leaf spring-like switching contact actuated by the transmission element snaps over the first time the dead point is passed over. In the region of the dead point, on the side of the contact surface on the switching contact, as a result of the offset of the clamping points there is always still sufficient contact force in order to carry the applied current safely. Furthermore, even in the event of extremely slow actuation of the switch, it is ensured that, until the switching point, there is sufficient contact force applied to the switching contact in order to carry the current of the electric motor. When the side of the switching contact that faces the transmission element snaps over, the side of the switching contact that faces the contact surface is also guided abruptly over its dead point and the circuit is reliably broken. Because of the bistable nature, impermissible switching to and fro of the contact system in the region of the switching point is also avoided.

Thus, the transmission element can be formed as a lever mounted on one side, a roller for guiding the belt being arranged on the end of the lever opposite the bearing. The transmission element is loaded in the direction of the switching contact by means of an elastic element, to be specific in particular by means of a tension spring. An arrangement of this type ensures immediate and undelayed switching of the contact system by the transmission element following the rupture of the belt.

In order to preserve the sensor against contamination and associated failure, the contact system can be arranged in a housing, the housing comprising a base and a cover latched to the base by means of latching/snap-action connections. The contact system is fixed to the base. For reasons of easy production, it is recommended to arrange the contact surface of the fixed contact on a carrier element and to injection mold the carrier element in the base. Likewise, the carrier parts of the switching contact can be injection molded in the base. The carrier element and the carrier part can project from the housing with their injection molded end in the manner of terminals, which means that separate terminals for the electrical feed lines to the sensor are rendered superfluous.

The free ends of the two limbs extending from the leaf spring can be clamped approximately centrally with respect to the leaf spring, on mutually opposite sides on the carrier part. As a result, a beneficial actuating travel until the contact system switches over is achieved. Of course, however, another division of the lengths of the two limbs of the leaf spring is also possible. The clamping point on the carrier part is expediently formed as a bearing notch in the manner of a knife edge bearing.

In further refinement, during its movement, the transmission element can act on an actuating element, which is mounted on the housing such that it can move, to be specific in particular in a housing attachment on the base. The actuating element then acts in turn by means of a pin on the second end of the leaf spring having the contact surface in order to switch the contact system. As a result, the housing with contact system and actuating element can be provided as a preassembled component, in order then to permit simple final installation in the entire subassembly for the sensor.

Since the contact system preferably operates in a bistable manner, renewed closing of the circuit is possible only by actuating a resetting element, for example in the manner of a reset knob, the danger of multiple switching in the limiting region being prevented effectively. In order once more to provide a component that can be preassembled, the resetting element can be mounted such that it can move, located opposite on the housing, to be specific in particular on a housing attachment on the base. The resetting element then likewise acts by means of a pin on the second end of the leaf spring having the contact surface for the purpose of switching over the contact system again.

It is recommended that the respective pin project through an opening in the housing attachment on the base in the direction of the second end of the leaf spring having the contact surface. In order to prevent the penetration of dust into the housing at the opening, the opening in the housing attachment can be sealed off by means of a seal surrounding the pin. In order that the actuating and the resetting element can be moved counter to an elastic force, a compression spring both for the actuating element and for the resetting element can finally be arranged on the respective housing attachment.

The advantages achieved by the invention, in addition to the improvements already cited, consist in particular in the fact that the sensor is less sensitive with respect to tolerances with regard to the length of the belt. In spite of the simple configuration, the sensor has a precisely defined switching point. When it switches over, the contact system carries out abrupt electrical opening between switching and fixed contacts, so that a changeover is achieved even in the case of welded contacts. Finally, even as compared with solutions with conventional switches, critical situations with regard to heating shortly before the switching point are reliably avoided. The sensor as claimed in the invention therefore operates in a more functionally reliable manner than previous sensors. In addition, the sensor can be produced economically.

BRIEF DESCRIPTION OF THE DRAWINGS

An exemplary embodiment of the invention is illustrated in the drawings and will be described in more detail in the following text. In the drawings.

DETAILED DESCRIPTION OF THE INVENTION

Figure 1:
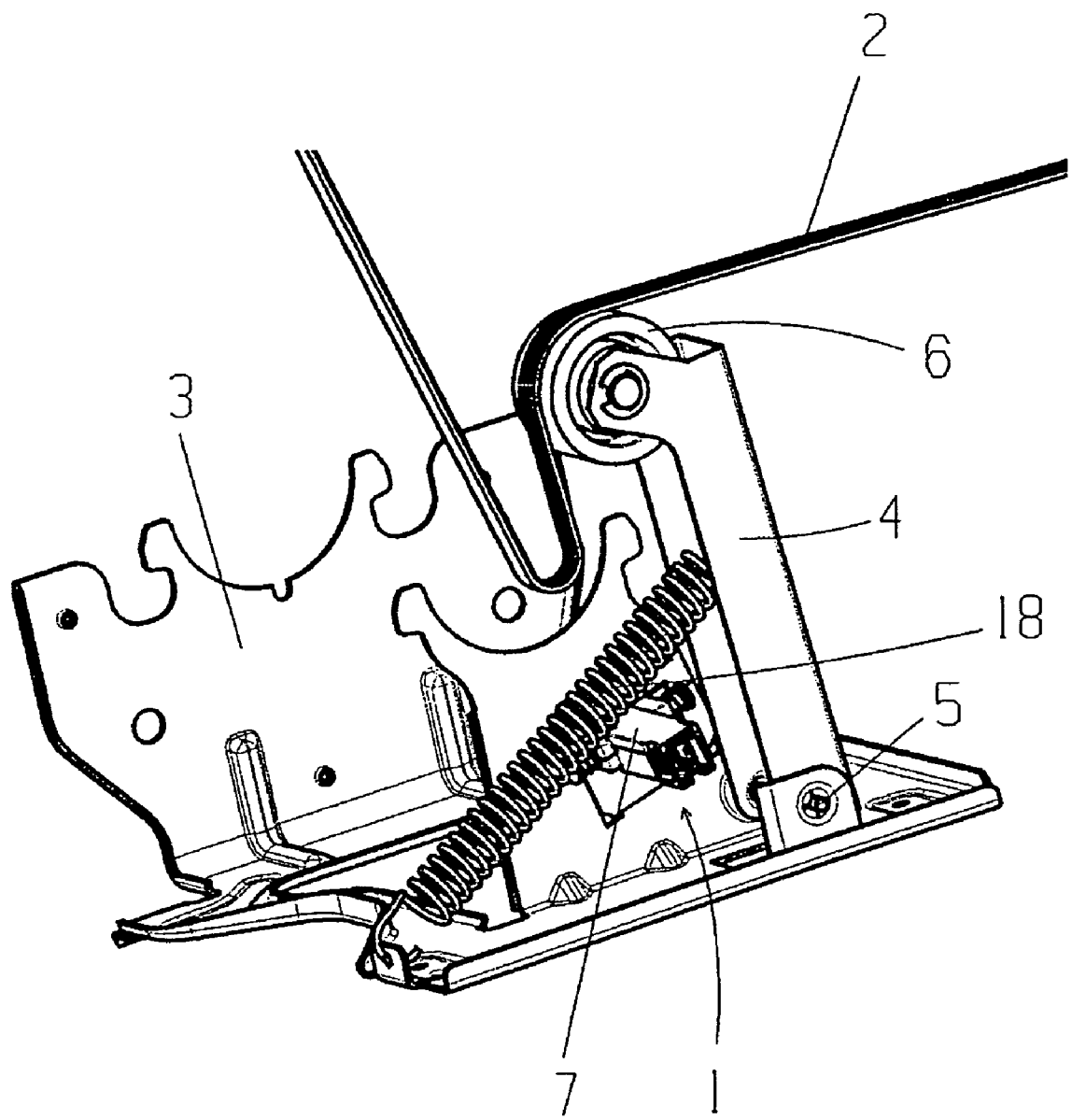
FIG. 1 shows a subassembly having a sensor for detecting a rupture in a belt for a domestic appliance in a perspective view.

In order to drive a drum in a tumble dryer, washing machine or another domestic appliance, use is made of an electric motor which moves the drum via a drive belt. In order to detect a rupture and/or an impermissible length change of the drive belt, use is made of a sensor 1 for detecting a rupture and/or a length change in a belt 2, as can be seen in FIG. 1.

The sensor 1 is fixed in a holder 3 in the domestic appliance, like the tumble dryer, the washing machine or the like. Arranged on the holder 3 is a movable transmission element 4 which is operatively connected to the belt 2. For this purpose, the transmission element 4 is formed as a lever mounted on one side on the holder 3 such that it can rotate. Arranged at the end of the lever of the transmission element 4 opposite the bearing 5 is a roller 6, on which the belt 2 is guided along. In the event of an impermissible length change and/or a rupture of the belt 2, the position of the transmission element 4 changes and, in the process, the latter acts on an electrical switch 7 having a contact system 8 that is visible in FIG. 3, in such a way that the contact system 8 switches over. The corresponding switching signal from the electrical switch 7 is then evaluated in order to detect the belt rupture or in relation to the length change of the belt 2.

Figure 3:
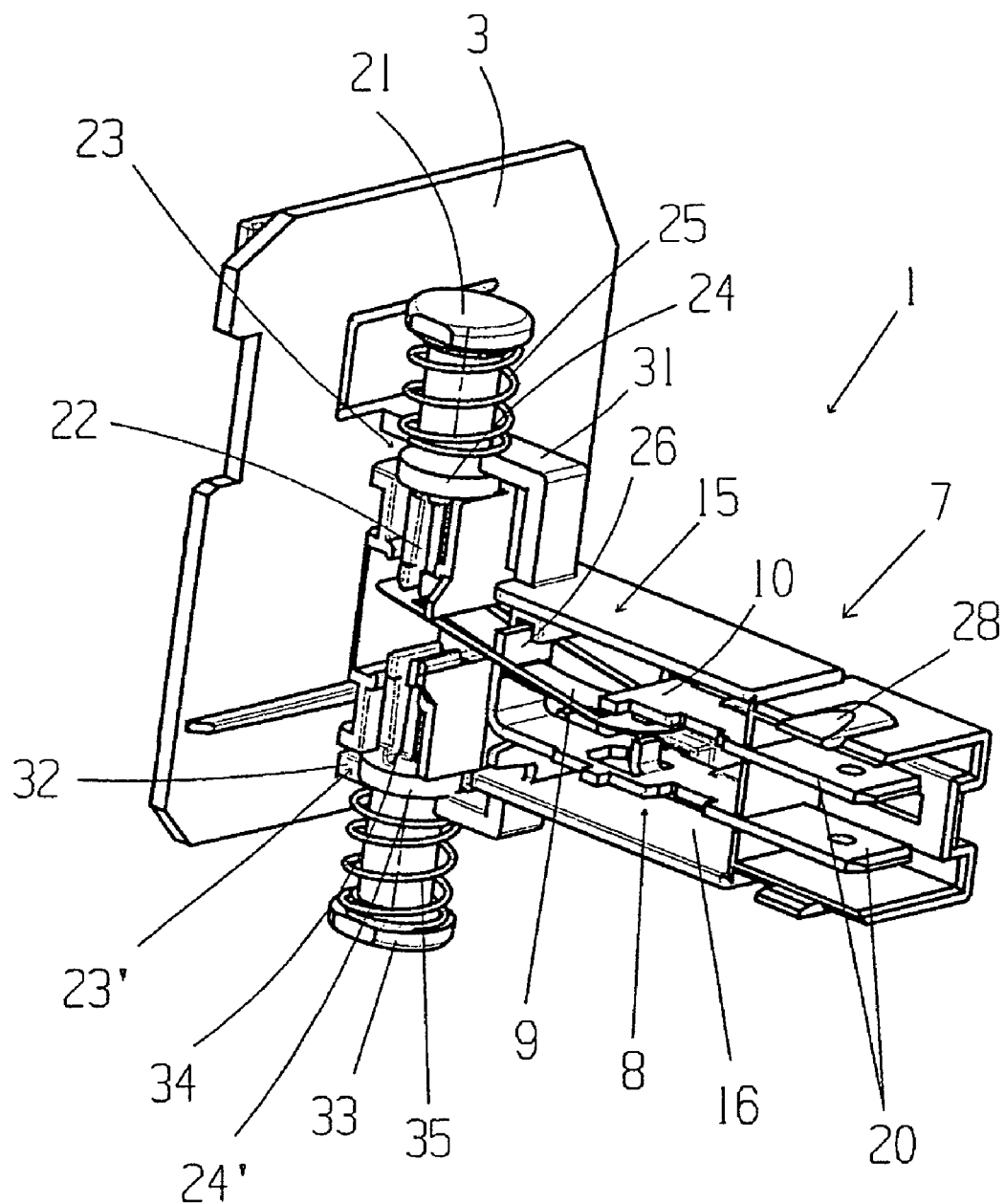
FIG. 3 shows the sensor as in FIG. 2 but with the cover removed and therefore the housing opened.
Figure 4:
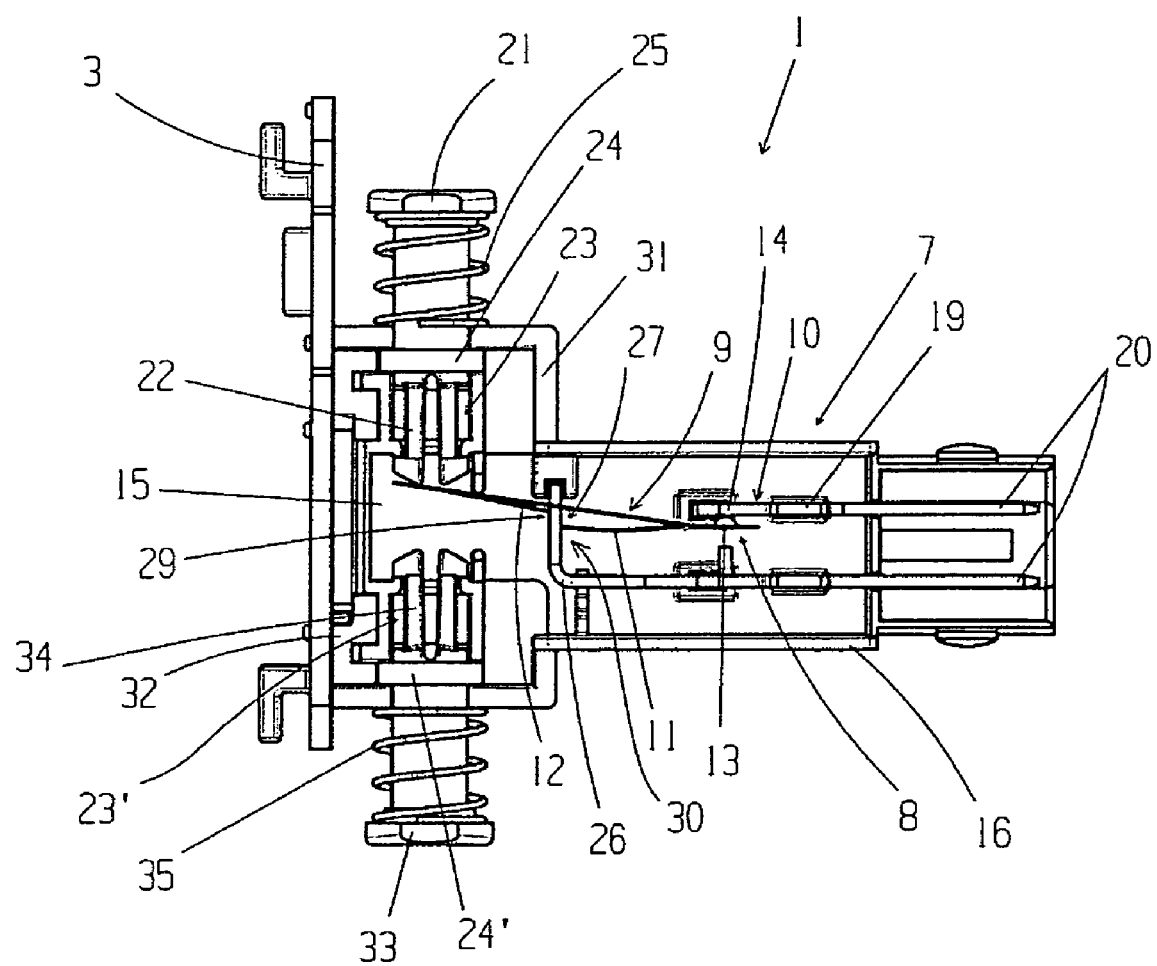
FIG. 4 shows the sensor from FIG. 2 in longitudinal section.

The construction of the sensor 1 can be seen in more detail in FIGS. 3 and 4. The contact system 8 comprises an electrically conductive leaf spring-like switching contact 9, the switching contact 9 being provided with a contact surface 13 (FIG. 4), and a corresponding contact surface 14 of an associated fixed contact 10. The contact surface 13 of the switching contact 9 is arranged on a first end of the switching contact 9, located on the right in FIG. 4. The transmission element 4 (FIG. 1) acts on the other, second end of the switching contact 9, located on the left in FIG. 4. A limb 11 that is free on one side extends approximately from the first end of the switching contact 9 in the direction of the second end. In turn, a further limb 12 free on one side extends from the second end of the switching contact 9 in the direction of the first end.

Figure 5:
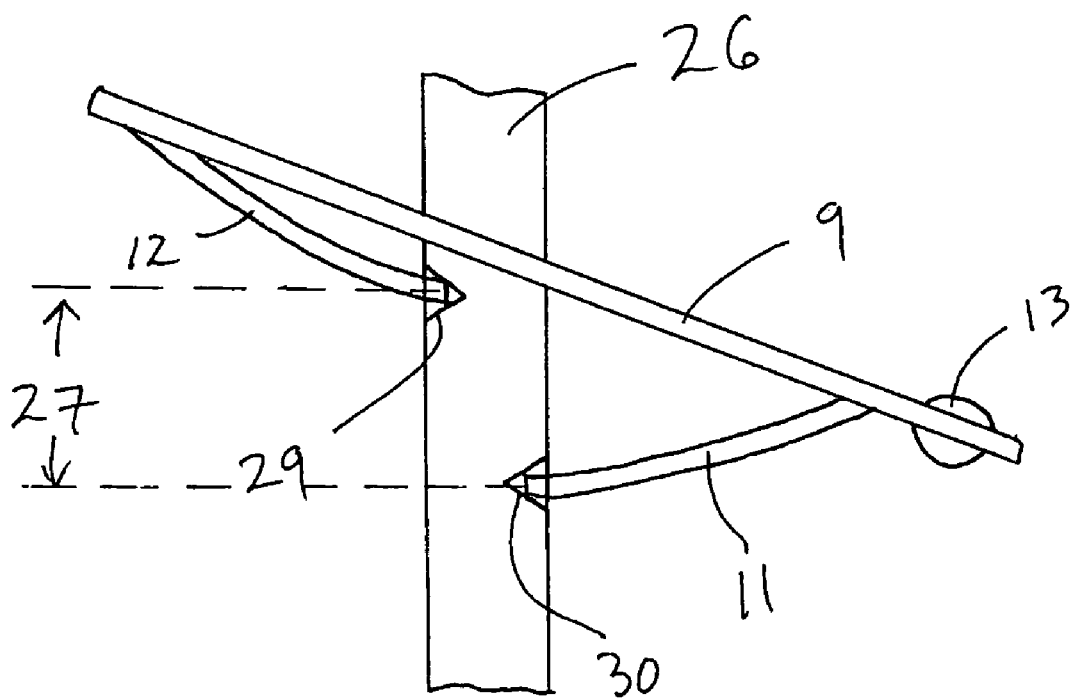
FIG. 5 is a magnified partial view showing the free ends of limbs 11 and 12 of switching contact 9 received in bearing notches 29 and 30 of carrier part 26.

As shown more clearly in FIG. 5, the free ends of the two limbs 11, 12 are in each case clamped with an offset 27 to a carrier part 26 of the switch 7. The free ends of the two limbs 11, 12 extending from the switching contact 9 are preferably clamped approximately centrally with respect to the switching contact 9, on mutually opposite sides of the carrier part 26, it being possible for the clamping points on the carrier part 26 to be formed as bearing notches 29, 30 in the manner of a knife edge bearing. As a result of action of the transmission element 4, the switching contact 9 of the contact system 8 then switches over in the manner of a cascade and, in particular, in a bistable manner, to separate contact surfaces 13 and 14.

As can be seen by means of FIG. 1, the transmission element 4 is loaded in the direction of the switching contact 9 by means of an elastic element, which is a tension spring 18. If, then, the belt 2 ruptures, the tension spring 18 pulls the transmission element 4 toward the electrical switch 7, which means that the contact system 8 of the latter switches over, as described.

Figure 2:
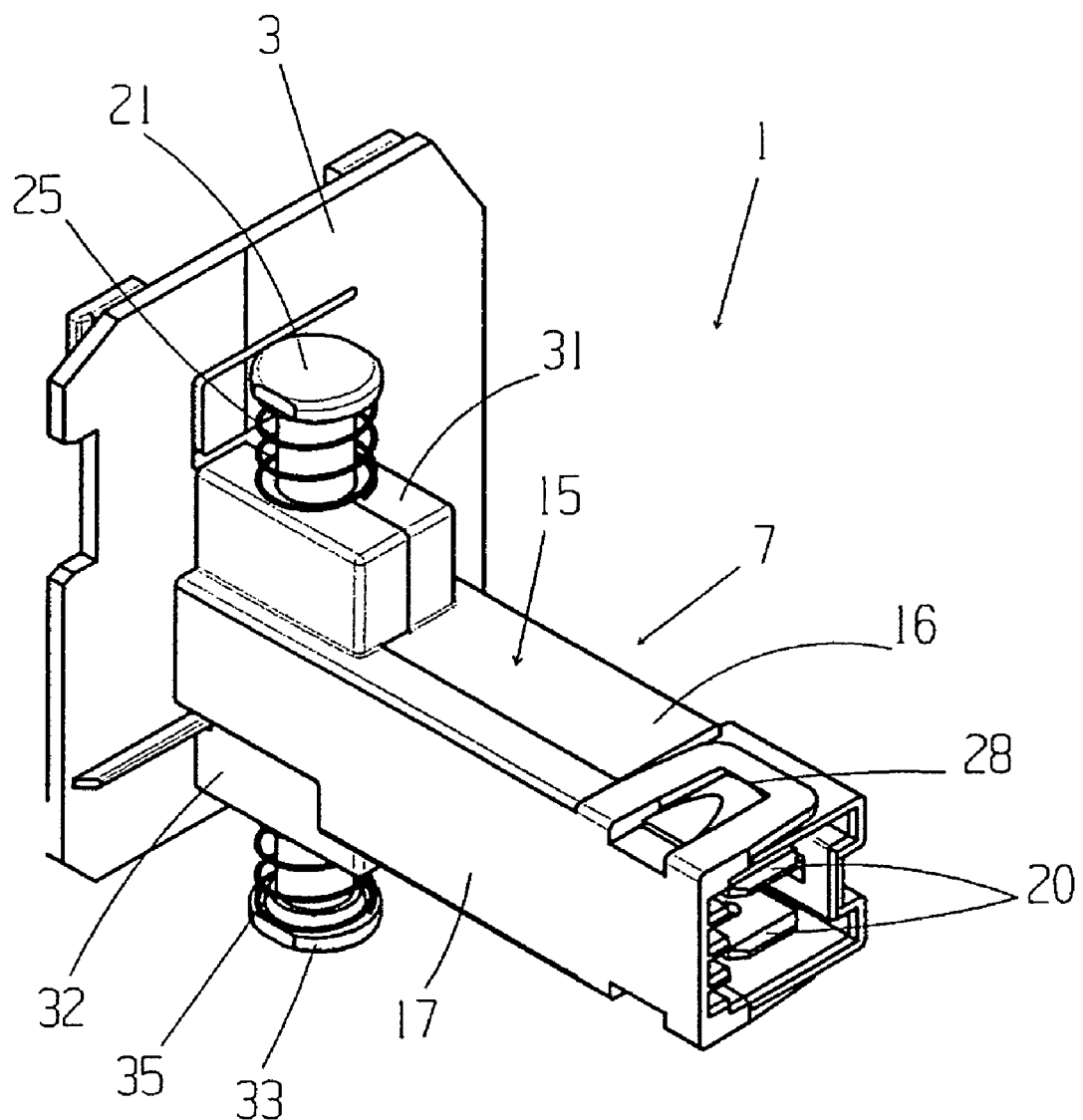
FIG. 2 shows the sensor from FIG. 1 in a perspective view.

The contact system 8 is arranged in a housing 15. As can be seen further in FIG. 2, the housing 15, which is composed of plastic, is assembled from a base 16 and a cover 17, the cover 17 being latched to the base 16 by means of latching/snap-action connections 28. The contact system 8 is fixed to the base 16. For this purpose, the carrier part 26 is injection molded into the base 16, by the carrier part 26 being encapsulated with the plastic used for the base of 16 during the production of the base 16 by injection molding. Referring to FIG. 4, the contact surface 14 for the fixed contact 10 is arranged on a carrier element 19. The carrier element 19 is likewise injection molded in the base 16. Both the carrier element 19 and the carrier part 26 in each case project out of the housing 15 with their injection molded end in the manner of electrical terminals 20, so that the electric feed lines can be fixed thereto.

During its movement, caused by the rupture or the length change of the belt 2, the transmission element 4 acts on an actuating element 21. The actuating element 21, configured in the manner of a plunger, is mounted in the housing 15, to be specific in a housing attachment 31 on the base 16, such that it can move counter to a compression spring 25 arranged on the housing attachment 31. In this case, the actuating element 21 then acts in turn on the second end of the switching contact 9 having the contact surface 13 for switching the contact system 8. For this purpose, the actuating element 21 has a pin 22, which projects through an opening 23 in the housing attachment 31 in the direction of the second end of the switching contact 9 having the contact surface 13.

Because of the bistable design of the contact system 8, the switch 7 is provided with a resetting element 33. The resetting element 33 is mounted on the housing 15, opposite the actuating element 21, to be specific on a housing attachment 32 on the base 16, such that it can move counter to a compression spring 35 arranged on the housing attachment 32. Once more by means of a pin 34, which likewise projects through an opening 23' in the housing attachment 32 in the direction of the second end of the switching contact 9, the resetting element 33 acts on the second end of the switching contact 9 having the contact surface 13 in order to switch over the contact system 8 again. By means of the resetting element 33, following a repair to the belt 2, the contact system 8 of the switch 7 can now be switched back manually, which means that the sensor 1 is again activated for the subsequent operation of the tumble dryer or the like.

In order to prevent the penetration of dirt, dust or the like into the housing 15, the openings 23, 23' in the housing attachment 31, 32 are sealed off by means of a seal 24, 24' surrounding the respective pin 22, 34. Sealing at the terminals 20 is achieved by these being injection molded into the base 16. The sensor 1 therefore operates in a failsafe manner even under the rough conditions of use in a tumble dryer, a washing machine or another domestic appliance.

The invention is not restricted to the exemplary embodiments described and illustrated. Instead, it comprises all expert developments within the scope of the invention defined by the patent claims. For example, a sensor 1 of this type can be used not only in domestic appliances, such as washing machines, tumble driers or the like, but also on other belt drives, for example of machine tools, of vehicles or the like.

LIST OF DESIGNATIONS

1: Sensor (for belt rupture)
2: Belt
3: Holder
4: Transmission element
5: Bearing (for transmission element)
6: Roller
7: Electrical switch
8: Contact system
9: Switching contact/leaf spring
10: Fixed contact
11,12: Free limb (on leaf spring)
13: Contact surface (of switching contact)
14: Contact surface (of fixed contact)
15: Housing
16: Base
17: Cover
18: Tension spring
19: Carrier element (of fixed contact)
20: Terminal
21: Actuating element
22: Pin (on actuating element)
23,23': Opening (in housing)
24,24': Seal
25: Compression spring (on actuating element)
26: Carrier part
27: Offset
28: Latching/snap-action connection
29,30: Bearing notch (on carrier part)
31,32: Housing attachment
33: Resetting element
34: Pin (on resetting element)
35: Compression spring (on resetting element)

What is claimed is:

1. A sensor for detecting at least one of a rupture and a length change in a belt, said sensor comprising:
    a movable transmission element operatively connected to the belt; and
    an electrical switch having a carrier part and a contact system, said contact system comprising:
        a switching contact having a leaf spring with a contact surface arranged on a first end of said leaf spring;
        a fixed contact operatively associated with said contact surface;
        a first limb free on one end extending approximately from a first end of said leaf spring in the direction of a second end;
        a second limb free on one end extending from the second end of said leaf spring in the direction of the first end;
        wherein the free ends of the first and second limbs are clamped offset from one another on said carrier part of said electrical switch; and
    wherein, in the event of at least one of a length change and a rupture of the belt, the transmission element acts on a second end of said leaf spring of said switching contact, such that said electrical switch switches over from a first state to a second state in the manner of a cascade.

2. The sensor of claim 1, wherein said electric switch changes from said first state to said second state in a bistable manner.

3. The sensor of claim 1, wherein said transmission element is comprised of a lever, a roller and a bearing, said roller being arranged on a first end of said lever, and said bearing being arranged on a second end of said lever opposite said roller, wherein the belt is guided on said roller and said transmission element is loaded in a direction toward said electrical switch by means of an elastic element.

4. The sensor of claim 3, wherein said elastic element comprises a tension spring.

5. The sensor of claim 1, wherein said contact system is arranged in a housing, said housing comprising a base and a cover, wherein said contact system is fixed to said base, and said cover is latched to said base by a means selected from a group consisting of latching and snap-action connections.

6. The sensor of claim 5, further comprising a contact surface for said fixed contact and a carrier element, wherein said contact surface of said fixed contact is arranged on said carrier element, said carrier element and said carrier part being injection molded in said base, said carrier element and said carrier part projecting out of said housing to form electrical terminals.

7. The sensor of claim 5, further comprising an actuating element comprising an actuating pin, said actuating element being movably mounted in a housing attachment on said base, wherein said transmission element acts on said actuating element, and said actuating element acts, by means of said actuating pin, on said second end of said leaf spring to switch said electrical switch from said first state to said second state.

8. The sensor of claim 7, further comprising a resetting element, said resetting element comprising a resetting pin being movably mounted in a housing attachment on said base opposite said actuating element, wherein said resetting element acts, by means of said resetting pin, on said second end of said leaf spring to switch said electrical switch from said second state to said first state.

9. The sensor of claim 8, wherein said resetting pin projects through an opening in said housing attachment on said base in the direction of the second end of said leaf spring and said opening is sealed by a second seal surrounding said resetting pin, and wherein said resetting element is moved counter to a compression spring arranged on said housing attachment.

10. The sensor of claim 7, wherein said actuating pin projects through an opening in said housing attachment on said base in the direction of the second end of said leaf spring and said opening is sealed by a first seal surrounding said actuating pin, and wherein said actuating element is moved counter to a compression spring arranged on said housing attachment.

11. The sensor of claim 1, wherein said free ends of said first and second limbs extending from said leaf spring are clamped on opposite sides of said carrier part.

12. The sensor of claim 11, wherein said free ends are clamped approximately centrally with respect to said leaf spring on said carrier part.

13. The sensor of claim 1, wherein a clamping point on said carrier part is formed as a bearing notch in the manner of a knife edge bearing.

14. The sensor of claim 1, wherein said movable transmission element is operatively connected to a drive belt of an electric motor disposed in an appliance selected from the group consisting of a tumble dryer and a washing machine.

15. A sensor for detecting at least one of a rupture and a length change in a drive belt of an electric motor disposed in an appliance selected from the group consisting of a tumble dryer and a washing machine, said sensor comprising:
   a movable transmission element operatively connected to the belt, said transmission element comprising a lever,
   a roller and a bearing, said roller being arranged on a first end of said lever, and said bearing being arranged on a second end of said lever opposite said roller, wherein the belt is guided on said roller; and
   an electrical switch having a carrier part and a contact system, said contact system comprising:
      a switching contact having a leaf spring with a contact surface arranged on a first end of said leaf spring;
      a fixed contact operatively associated with said contact surface;
      a first limb free on one end extending approximately from a first end of said leaf spring in the direction of a second end;
      a second limb free on one end extending from the second end of said leaf spring in the direction of the first end;
      wherein the free ends of the first and second limbs are clamped offset from one another on said carrier part of said electrical switch; and
   an elastic element for loading said transmission element in a direction toward said electrical switch;
   wherein, in the event of at least one of a length change and a rupture of the belt, the transmission element acts on a second end of said leaf spring of said switching contact, such that said electrical switch switches over from a first state to a second state in the manner of a cascade.

16. A sensor for detecting at least one of a rupture and a length change in a belt, said sensor comprising:
   a movable transmission element operatively connected to the belt; and
   an electrical switch having a carrier part and a contact system, said contact system comprising:
      a switching contact having a leaf spring with a contact surface arranged on a first end of said leaf spring;
      a fixed contact operatively associated with said contact surface;
      a first limb free on one end extending approximately from a first end of said leaf spring in the direction of a second end, wherein said free end of said first limb is clamped in a first bearing notch on a first side of said carrier part to form a knife edge bearing;
      a second limb free on one end extending from the second end of said leaf spring in the direction of the first end, wherein said free end of said second limb is clamped in a second bearing notch on a second side of said carrier part to form a knife edge bearing, said first and second bearing notches being offset from one another on said carrier part of said electrical switch; and
   wherein, in the event of at least one of a length change and a rupture of the belt, the transmission element acts on a second end of said leaf spring of said switching contact, such that said electrical switch switches over from a first state to a second state in the manner of a cascade.

* * * * *